(12) United States Patent
Sadeghi

(10) Patent No.: US 12,089,944 B2
(45) Date of Patent: *Sep. 17, 2024

(54) METHOD AND SYSTEM FOR NEUROHYDRODISSECTION

(71) Applicant: Payman Sadeghi, Houston, TX (US)

(72) Inventor: Payman Sadeghi, Houston, TX (US)

(73) Assignee: Payman Sadeghi, Houston, TX (US)

( * ) Notice: Subject to any disclaimer, the term of this patent is extended or adjusted under 35 U.S.C. 154(b) by 918 days.

This patent is subject to a terminal disclaimer.

(21) Appl. No.: 17/150,086

(22) Filed: Jan. 15, 2021

(65) Prior Publication Data

US 2021/0128050 A1    May 6, 2021

Related U.S. Application Data

(63) Continuation of application No. 16/589,658, filed on Oct. 1, 2019, now Pat. No. 10,932,711, which is a
(Continued)

(51) Int. Cl.
*A61B 5/00*    (2006.01)
*A61B 8/08*    (2006.01)
(Continued)

(52) U.S. Cl.
CPC .......... *A61B 5/4029* (2013.01); *A61B 5/0053* (2013.01); *A61B 8/0841* (2013.01);
(Continued)

(58) Field of Classification Search
CPC .......... A61M 5/00; A61M 5/178; A61M 5/30; A61M 5/3007; A61M 5/42; A61M 5/422;
(Continued)

(56) References Cited

U.S. PATENT DOCUMENTS

| | | |
|---|---|---|
| 5,443,850 A | 8/1995 | Thys-Jacobs |
| 5,676,691 A | 10/1997 | Friedman |
| (Continued) | | |

FOREIGN PATENT DOCUMENTS

| | | |
|---|---|---|
| CA | 2877022 A1 | 1/2014 |
| CN | 104704111 A | 6/2015 |
| (Continued) | | |

OTHER PUBLICATIONS

Bright et al., Migraine and tension-type headache treated with stromal vascular fraction: a case series, 2014, Journal of Medical Case Reports 2014, 8:237 http://www.jmedicalcasereports.com/content/8/1/237, 5 pages (Year: 2014).
(Continued)

*Primary Examiner* — Kami A Bosworth
*Assistant Examiner* — Alexandra Lalonde
(74) *Attorney, Agent, or Firm* — Dickinson Wright PLLC

(57) ABSTRACT

A method of neurohydrodissection for reducing a perception of pain in a patient is disclosed. The method comprises a step of physically inspecting the patient and locating a first compression site of a nerve of the patient where the nerve passes through a tissue and is inflamed. The method comprises a step of imaging the patient at the first compression site. The method comprises a step of inserting a syringe at the first compression site, wherein while the imaging the patient at the first compression site occurs, guiding the syringe to an intersection between the nerve and the tissue, injecting a solution with the syringe at the intersection and dissecting the nerve from the tissue.

23 Claims, 12 Drawing Sheets

Related U.S. Application Data continuation-in-part of application No. 15/907,074, filed on Feb. 27, 2018, now Pat. No. 10,456,419.

(60) Provisional application No. 62/871,405, filed on Jul. 8, 2019, provisional application No. 62/600,726, filed on Feb. 27, 2017.

(51) Int. Cl.
  *A61B 17/3203* (2006.01)
  *A61M 5/178* (2006.01)
  *A61M 13/00* (2006.01)

(52) U.S. Cl.
  CPC ......... *A61B 17/3203* (2013.01); *A61M 5/178* (2013.01); *A61M 13/00* (2013.01)

(58) Field of Classification Search
  CPC .... A61M 5/427; A61M 13/00; A61M 13/003; A61M 13/006; A61M 16/01; A61M 19/00; A61M 39/00; A61M 2202/00; A61M 2202/0007; A61M 2202/0241; A61M 2202/02; A61M 2202/048; A61M 2210/083; A61M 2210/06; A61M 2210/08; A61B 5/4029; A61B 5/24; A61B 5/0053; A61B 5/4041; A61B 5/4893; A61B 5/6877; A61B 5/4824; A61B 5/4827; A61B 6/506; A61B 17/3203; A61B 17/32037; A61B 2018/00434; A61N 1/0551; A61N 1/36021; A61N 1/0568

See application file for complete search history.

(56) References Cited

U.S. PATENT DOCUMENTS

| | | | |
|---|---|---|---|
| 5,977,145 | A | 11/1999 | Silberstein et al. |
| 6,432,986 | B2 | 8/2002 | Levin |
| 6,735,475 | B1 | 5/2004 | Whitehurst et al. |
| 7,601,707 | B1 | 10/2009 | Minks |
| 7,704,511 | B2 | 4/2010 | Turkel et al. |
| 8,198,240 | B2 | 6/2012 | Yeomans et al. |
| 8,202,838 | B2 | 6/2012 | Yeomans et al. |
| 8,252,745 | B2 | 8/2012 | Yeomans et al. |
| 8,501,691 | B2 | 8/2013 | Yeomans et al. |
| 8,562,973 | B2 | 10/2013 | Edinger et al. |
| 8,617,571 | B2 | 12/2013 | Blumenfeld |
| 8,691,769 | B2 | 4/2014 | Borodic et al. |
| 8,828,376 | B2 | 9/2014 | Zeitlin et al. |
| 8,889,151 | B2 | 11/2014 | Turkel et al. |
| 9,078,893 | B2 | 7/2015 | Turkel et al. |
| 9,205,258 | B2 | 12/2015 | Simon et al. |
| 9,248,168 | B2 | 2/2016 | Blumenfeld |
| 9,656,074 | B2 | 5/2017 | Simon et al. |
| 9,713,543 | B2 | 7/2017 | Koo |
| 9,814,616 | B2 | 11/2017 | Koo |
| 9,827,297 | B2 | 11/2017 | Blumenfeld |
| 9,895,530 | B2 | 2/2018 | Boggs, II et al. |
| 9,901,626 | B2 | 2/2018 | Lamb |
| 10,363,419 | B2 | 7/2019 | Simon et al. |
| 10,932,711 | B2 * | 3/2021 | Sadeghi .............. A61B 17/3203 |
| 2009/0252764 | A1 | 10/2009 | Blumenfeld |
| 2011/0087173 | A1 * | 4/2011 | Sibbitt, Jr. ......... A61B 10/0233 604/207 |
| 2012/0101479 | A1 | 4/2012 | Paspaliaris et al. |
| 2012/0164113 | A1 | 6/2012 | Victor |
| 2013/0189234 | A1 | 7/2013 | Victor |
| 2013/0245504 | A1 | 9/2013 | Jou |
| 2014/0017209 | A1 | 1/2014 | Aberman et al. |
| 2014/0025039 | A1 * | 1/2014 | Rajendran ............. A61M 19/00 604/512 |
| 2014/0058252 | A1 * | 2/2014 | Varav .................. A61M 1/7415 604/28 |
| 2014/0079687 | A1 | 3/2014 | Blumenfeld |
| 2015/0159151 | A1 | 6/2015 | Bright et al. |
| 2015/0174172 | A1 | 6/2015 | Bright et al. |
| 2016/0030408 | A1 | 2/2016 | Levin |
| 2016/0030488 | A1 | 2/2016 | Fischkoff et al. |
| 2016/0151468 | A1 | 6/2016 | Blumenfeld |

FOREIGN PATENT DOCUMENTS

| | | |
|---|---|---|
| CN | 104902909 A | 9/2015 |
| EP | 2282766 B1 | 11/2011 |
| EP | 2392344 A1 | 12/2011 |
| EP | 2863927 A1 | 4/2015 |
| JP | 2015521630 A | 7/2015 |
| KR | 20090024277 A | 3/2009 |
| KR | 20150091037 A | 8/2015 |
| WO | 2012127320 A1 | 9/2012 |
| WO | 2013138786 A1 | 9/2013 |
| WO | 2014000029 A1 | 1/2014 |
| WO | 2014000031 A1 | 1/2014 |
| WO | 2014099423 A1 | 6/2014 |
| WO | 2014146082 A1 | 9/2014 |
| WO | 2015079319 A1 | 4/2015 |
| WO | 2017044904 A1 | 3/2017 |

OTHER PUBLICATIONS

Mauskop et al., Stem Cells in the Treatment of Refractory Chronic Migraines, 2017, Case Rep Neurol 9:149-155 (Year 2017).

Cass, S.P., Ultrasound-Guided Nerve Hydrodissection: What is it? A Review of the Literature, Jan. 2016, Current Sports Medicine Reports 15(1):20-22 (Year: 2016).

Lam et al., Transition from Deep Regional Blocks toward Deep Nerve Hydrodissection in the Upper Body and Torso: Method Description . . . , 2017, BioMed Research International vol. 2017, Article ID 7920438, 17 Pages (Year: 2017).

* cited by examiner

METHOD AND SYSTEM FOR NEUROHYDRODISSECTION

CROSS-REFERENCE TO RELATED APPLICATIONS

This application is a continuation of U.S. patent application Ser. No. 16/589,658, filed on Oct. 1, 2019, which issued as U.S. Pat. No. 10,932,711 on Mar. 2, 2021, which claims the benefit of U.S. Provisional Patent Application No. 62/871,405 filed Jul. 8, 2019, and is a continuation-in-part of U.S. patent application Ser. No. 15/907,074, filed Feb. 27, 2018, which issued as U.S. Pat. No. 10,456,419 on Oct. 29, 2019, which claims the benefit of U.S. Provisional Patent Application No. 62/600,726 filed on Feb. 27, 2017, the entire disclosures of which are hereby incorporated by reference for all purposes.

TECHNICAL FIELD

The present disclosure relates generally to treating headaches. Specifically, this disclosure relates to a system and method for neurohydrodissection for treating all types of headaches by applying injections at inflamed nerves of the peripheral nervous system of a patient.

BACKGROUND

Headaches can be a debilitating problem for people who suffer them. For example, there are estimations that up to 15% of people globally are affected by migraine headaches. Migraine headaches are typically recurrent, often start during puberty, and can worsen during middle age. The symptoms may be quite severe and may include nausea, vomiting, and sensitivity to outside influences such as light, sound, or even smell. Unfortunately, migraines can be long lasting, sometimes up to three or more days. Accordingly, improvements in headache treatments continue to be of interest.

SUMMARY

This section provides a general summary of the present disclosure and is not a comprehensive disclosure of its full scope or all of its features, aspects, and objectives.

Disclosed herein is method of neurohydrodissection for reducing a perception of pain in a patient. The method comprises the step of physically inspecting a patient and locating a first compression site of a nerve of the patient where the nerve passes through a tissue and is inflamed. The method comprises the step of imaging the patient at the first compression site. The method comprises the step of inserting a syringe at the first compression site, wherein while the first compression site is being imaged, guiding the syringe to an intersection between the nerve and the tissue, injecting a solution with the syringe at the intersection and dissecting the nerve from the tissue.

Also disclosed herein is a method of neurohydrodissection for reducing a perception of pain. The method comprises the step of physically inspecting a patient and locating a first compression site of a nerve of the patient where the nerve passes through at least one of muscle, fascia, and ligament and the nerve is inflamed. The method comprises the step of imaging the patient at the first compression site. The method comprises the step of inserting a syringe at the first compression site, wherein while the first compression site is being imaged, guiding the syringe to an intersection between the nerve and the at least one of the muscle, fascia, and ligament, injecting a solution with the syringe at the intersection and dissecting the nerve from the at least one of the muscle, fascia, and ligament. The method comprises repeating at least some of the above steps for a second compression site.

Disclosed herein is a method of neurohydrodissection for treating a headache in a patient. The method comprises the step of physically inspecting a patient and locating a first compression site of a nerve of the patient where the nerve passes through a tissue and is inflamed. The method comprises the step of ultrasound imaging the patient at the first compression site. The method comprises the step of inserting a syringe at the first compression site, wherein while the first compression site is being imaged, guiding the syringe to an intersection between the nerve and the tissue, injecting a solution with the syringe at the intersection and dissecting the nerve from the tissue. The method comprises the step of confirming with the patient whether a headache symptom has changed.

Also disclosed herein is a method of neurohydrodissection for treating a headache in a patient. The method comprises the step of physically inspecting a patient and locating a first compression site of a nerve of the patient where the nerve passes through at least one of muscle, fascia, and ligament and is inflamed. The method comprises the step of ultrasound imaging the patient at the first compression site. The method comprises the step of inserting a syringe at the first compression site, wherein while the first compression site is being imaged, guiding the syringe to an intersection between the nerve and the at least one of the muscle, fascia, and ligament, injecting a solution with the syringe at the intersection and dissecting the nerve from the at least one of the muscle, fascia, and ligament. The method comprises the step of confirming with the patient whether a headache symptom has changed. The method comprises repeating at least some of the above steps for a second compression site.

Also disclosed herein is a method of neurohydrodissection for treating a symptom in a patient. The method comprises the step of inspecting a patient and locating a first compression site of a nerve that is inflamed. The method comprises the step of imaging the patient at the first compression site. The method includes the step of inserting a syringe at the first compression site, wherein the syringe includes a solution comprising dextrose 5% in water (D5W). The method includes the step of guiding the syringe to a first intersection of between the nerve and the at least one of the muscle, fascia, and ligament. The method includes the step of injecting the solution with the syringe at the first intersection. The method includes the step of dissecting the nerve from the at least one of the muscle, fascia, and ligament to form a gap. The method includes the step of confirming with the patient whether the symptom has changed. The method includes the step of repeating at least some of the above steps for a second compression site of the nerve.

Other technical features may be readily apparent to one skilled in the art from the following figures, descriptions, and claims.

Before undertaking the DETAILED DESCRIPTION below, it may be advantageous to set forth definitions of certain words and phrases used throughout this patent document. The terms "include" and "comprise," as well as derivatives thereof, mean inclusion without limitation. The term "or" is inclusive, meaning and/or. The phrase "at least one of," when used with a list of items, means that different combinations of one or more of the listed items may be used, and only one item in the list may be needed. For example, "at least one of: A, B, and C" includes any of the following combinations: A, B, C; A and B; A and C; B and C; and A and B and C.

Definitions for other certain words and phrases are provided throughout this patent document. Those of ordinary skill in the art should understand that in many if not most instances, such definitions apply to prior as well as future uses of such defined words and phrases.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

Figure 1A:
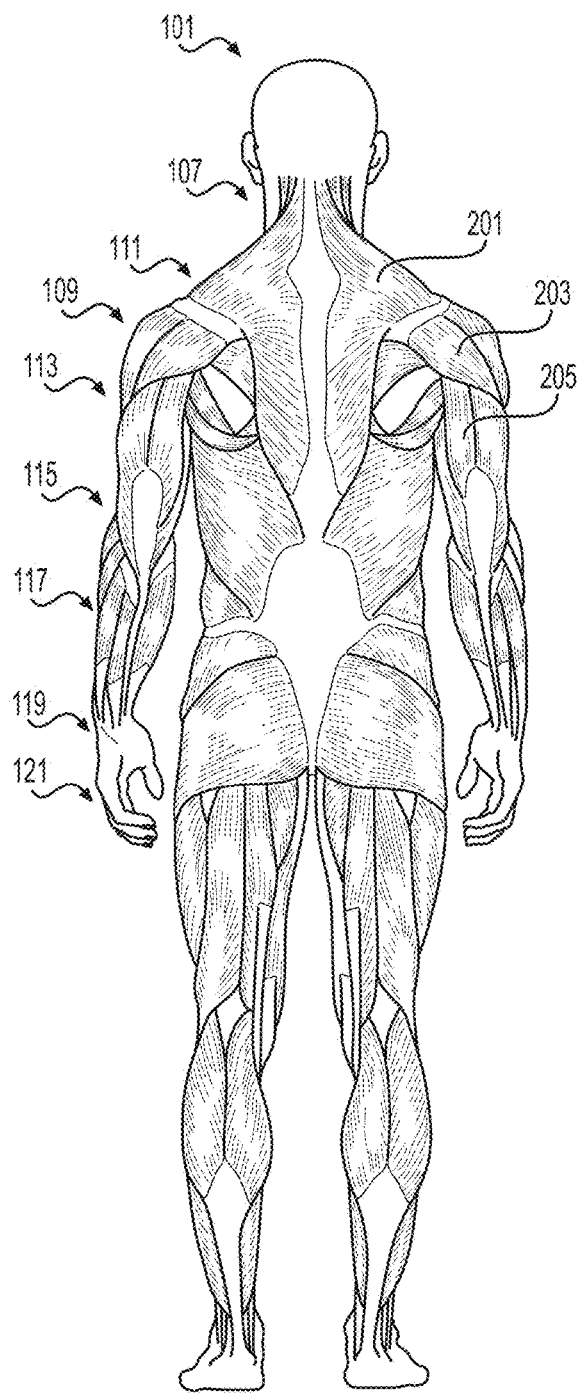
FIGS. 1A and 1B are schematic illustrations of a patient with exemplary embodiments of potential compression sites of median nerves in arms of the patient in accordance with aspects of the present disclosure.
Figure 1B:
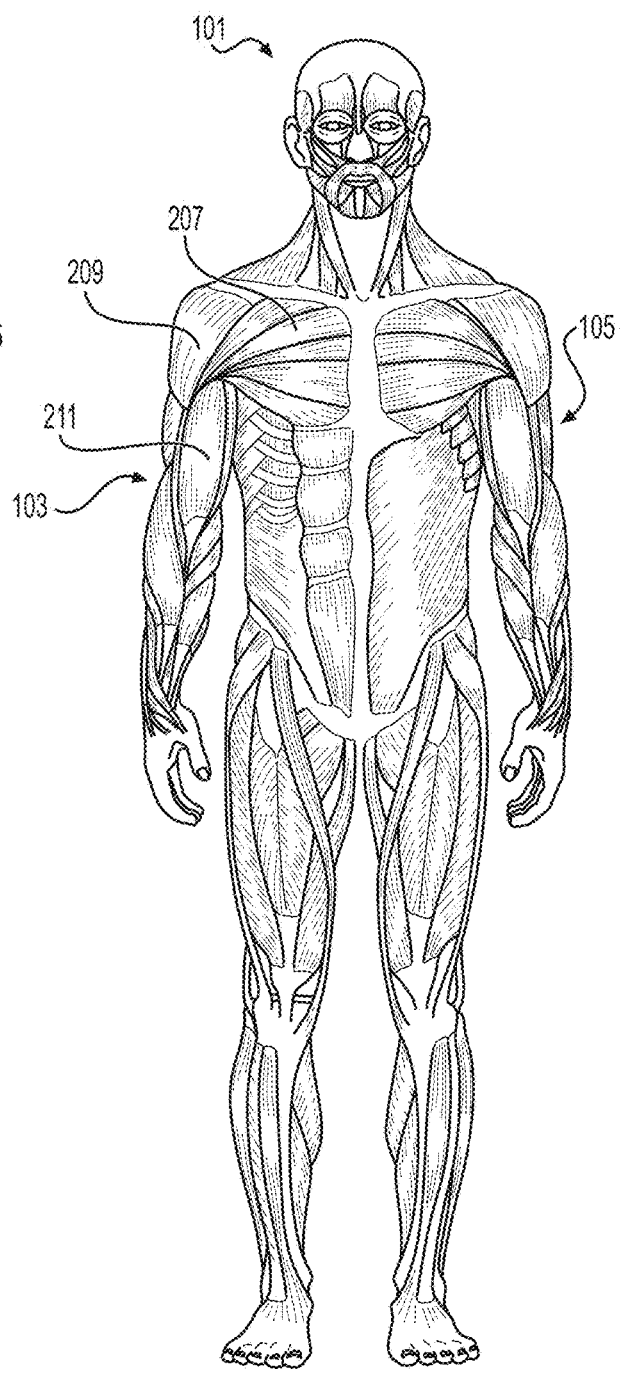

FIGS. 1 through 8, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system or device.

The underlying mechanisms of some headaches, such as migraine headaches (or migraines) are not fully known, but most current theories for the cause of migraines are central (i.e., thought to involve the nerves and blood vessels of the brain). Embodiments of the present disclosure treat headaches as a peripheral nerve system disorder (i.e., involving nerves and blood vessels outside of the brain) and not a central one. Limiting treatment of patients having headache symptoms by treating only the peripheral nervous systems of the patients (rather than the patients' central nervous systems) contradicts conventionally accepted practices of treating only the central nervous systems of the patients for headaches. Thus, in some embodiments, the treated nerve is not in the central nervous system of the patient; rather, the nerve can be in a peripheral nervous system of the patient. The treated nerve can be in the somatic nervous system of the peripheral nervous system of the patient.

Accordingly, the present disclosure can use injection treatments to repair inflamed nerves. For example, embodiments of a method of neurohydrodissection for preventing and/or treating a headache in a patient are disclosed. In the simplified, schematic views of FIGS. 1A, 1B and 2, the nerves of a patient 101 include median nerves 103, 105. Each median nerve 103, 105 extends from a neck 107, through a shoulder 109, adjacent a shoulder blade 111 (FIG. 1A; in the mid to upper back), and down an upper arm 113, an elbow 115, a forearm 117, a wrist 119, and a hand 121 of the patient 101. Although median nerves 103, 105 are shown and described, other nerves of the patient 101 may also be treated.

Each median nerve 103, 105 can have one or more compression sites 201-217 in the patient 101. As used herein, the term "compression site" of a nerve can be defined as the location in the patient 101 where the nerve 103 is, for example, changing course or direction and/or passes through body tissue, or tissue 133, of the patient 101. Such body tissue 133 can include at least one of muscle 141, fascia 143 (e.g., fascia lining of the tissue), and ligament where the nerve 103 is inflamed. In another embodiment, compression sites can be treated throughout the body to lessen or eliminate symptoms, such as pain symptoms.

Figure 2:
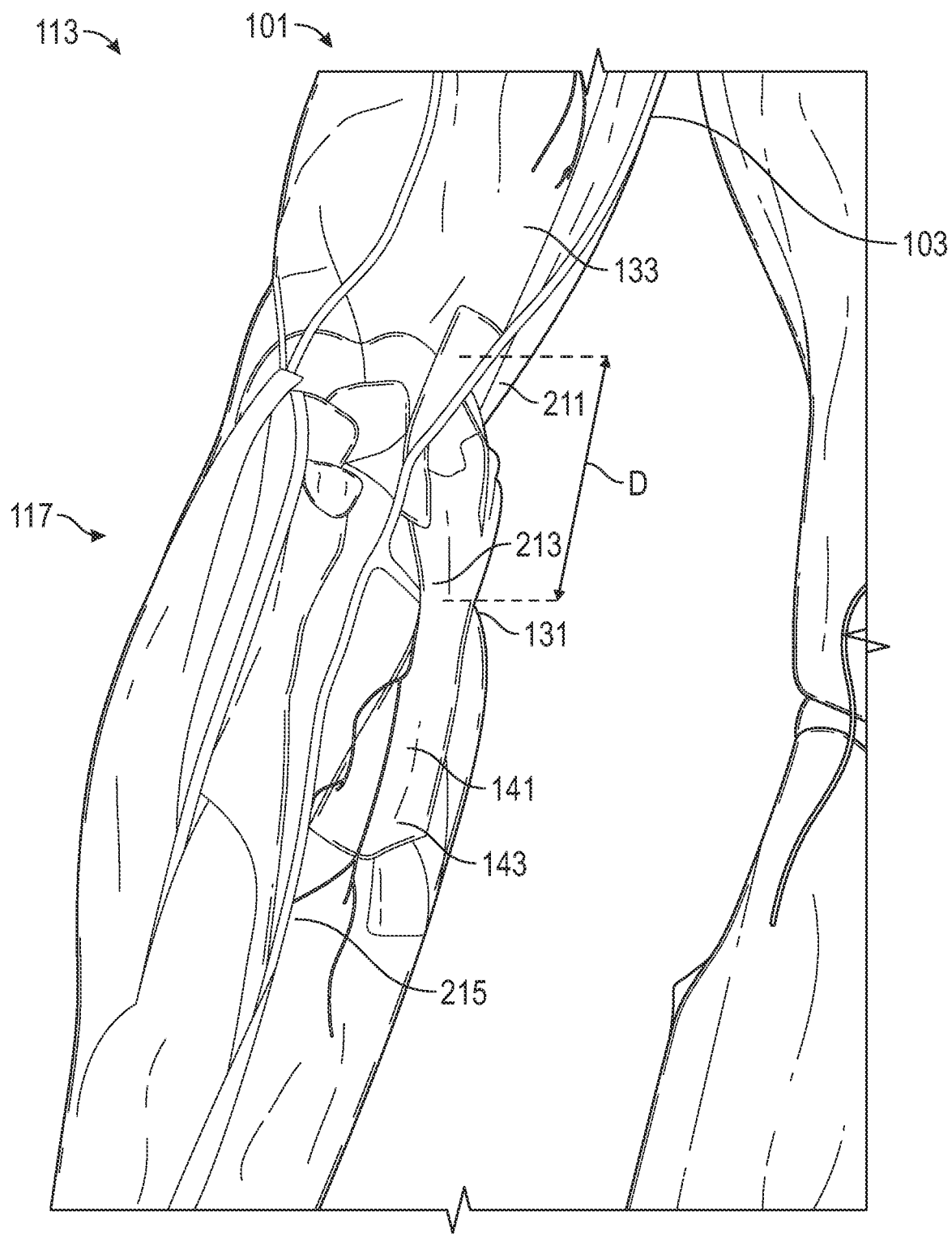
FIG. 2 is a schematic illustration of an arm of the patient with exemplary embodiments of potential compression sites in the arm in accordance with aspects of the present disclosure.
Figure 3:
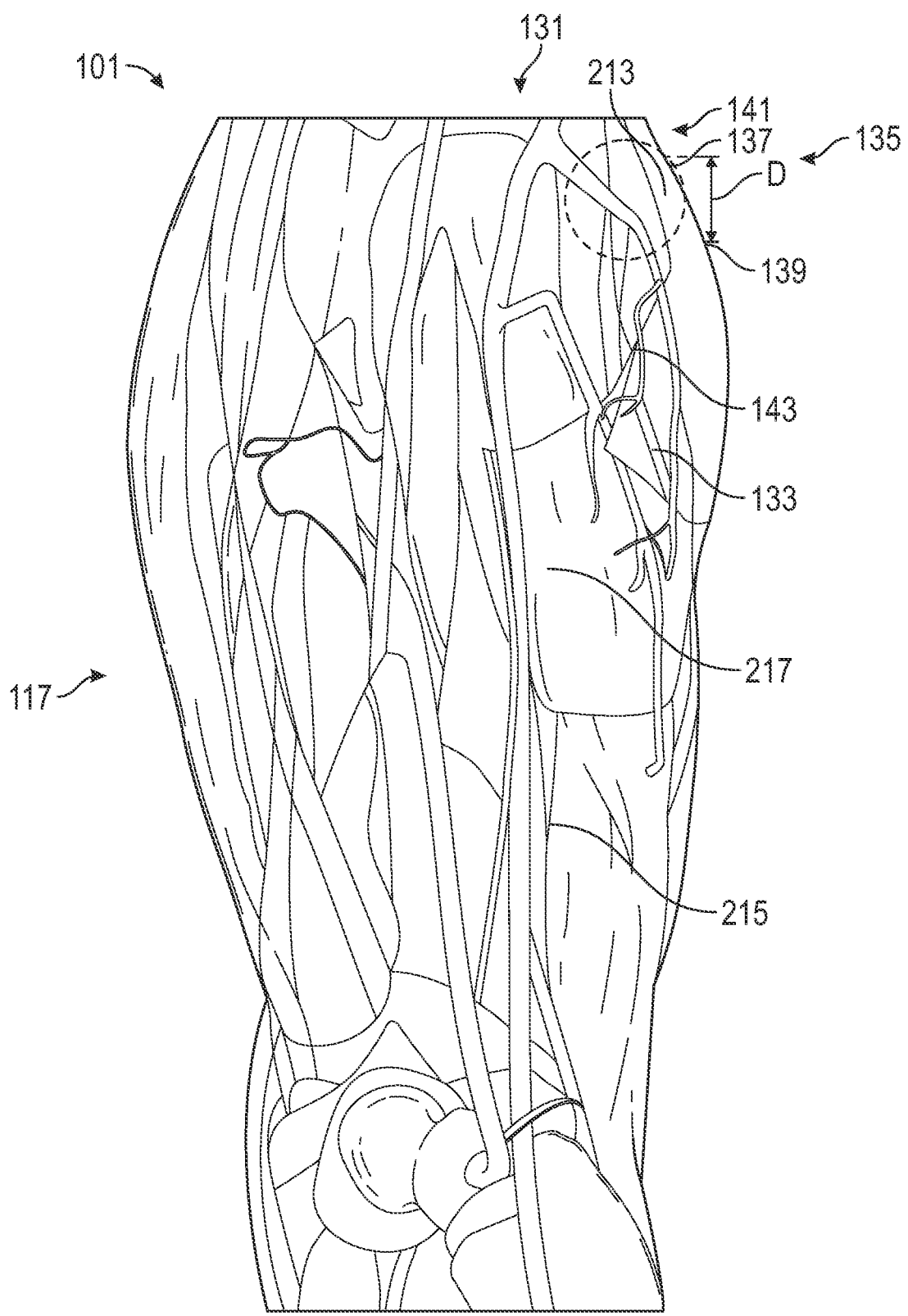
FIG. 3 is an enlarged, schematic illustration of a nerve in an arm of the patient with a potential compression sites along the nerve in accordance with aspects of the present disclosure.
Figure 4:
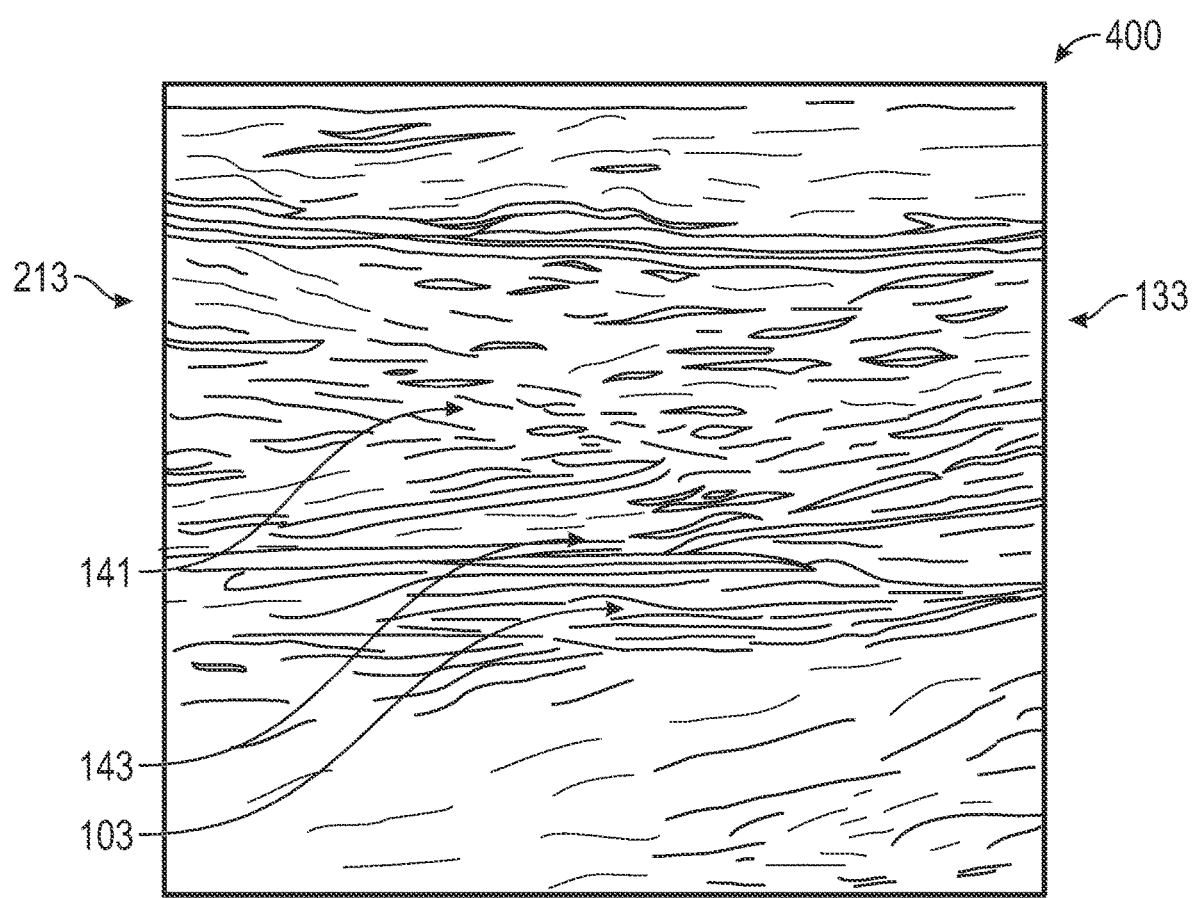
FIG. 4 is an ultrasound image of a procedure in a process of treating a compression site in accordance with aspects of the present disclosure.
Figure 5:
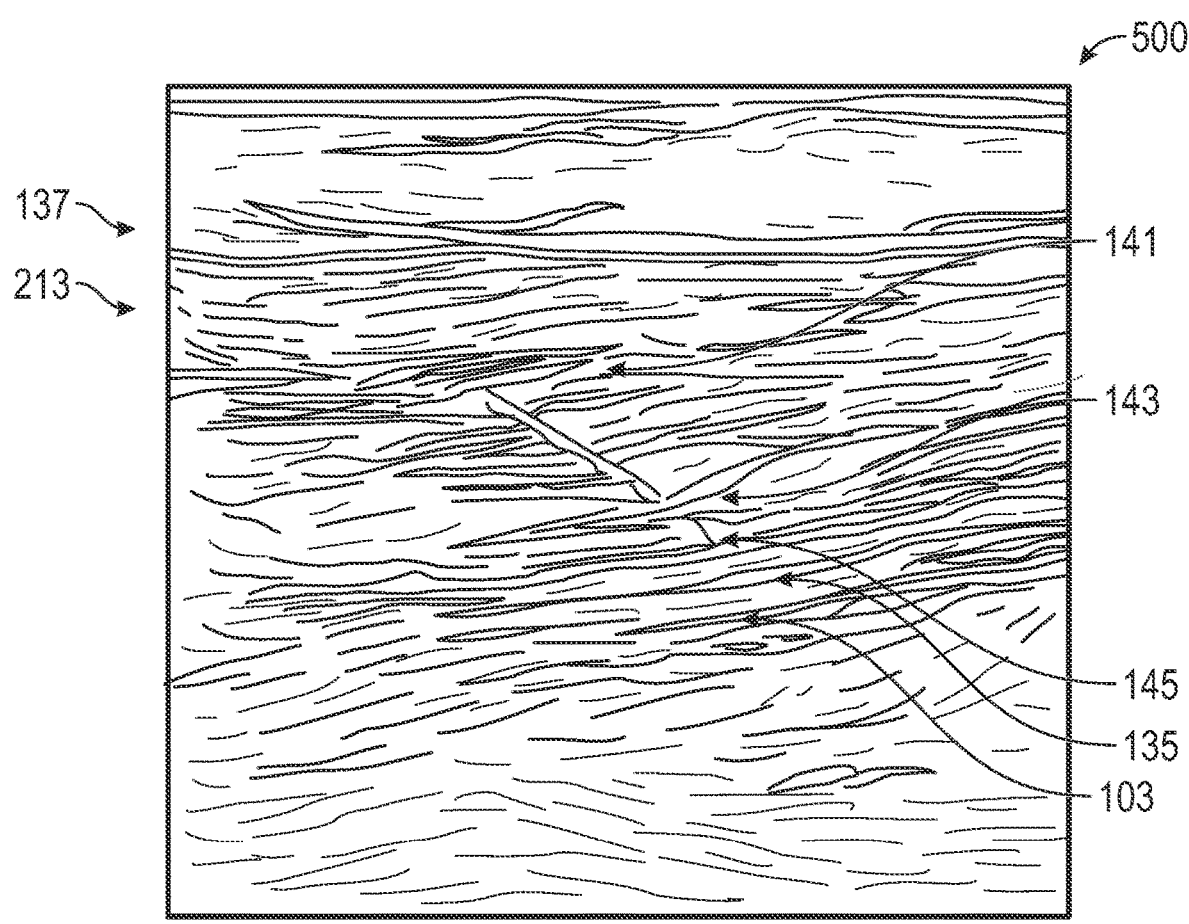
FIG. 5 is an ultrasound image of a procedure in a process of treating a compression site in accordance with aspects of the present disclosure.
Figure 6:
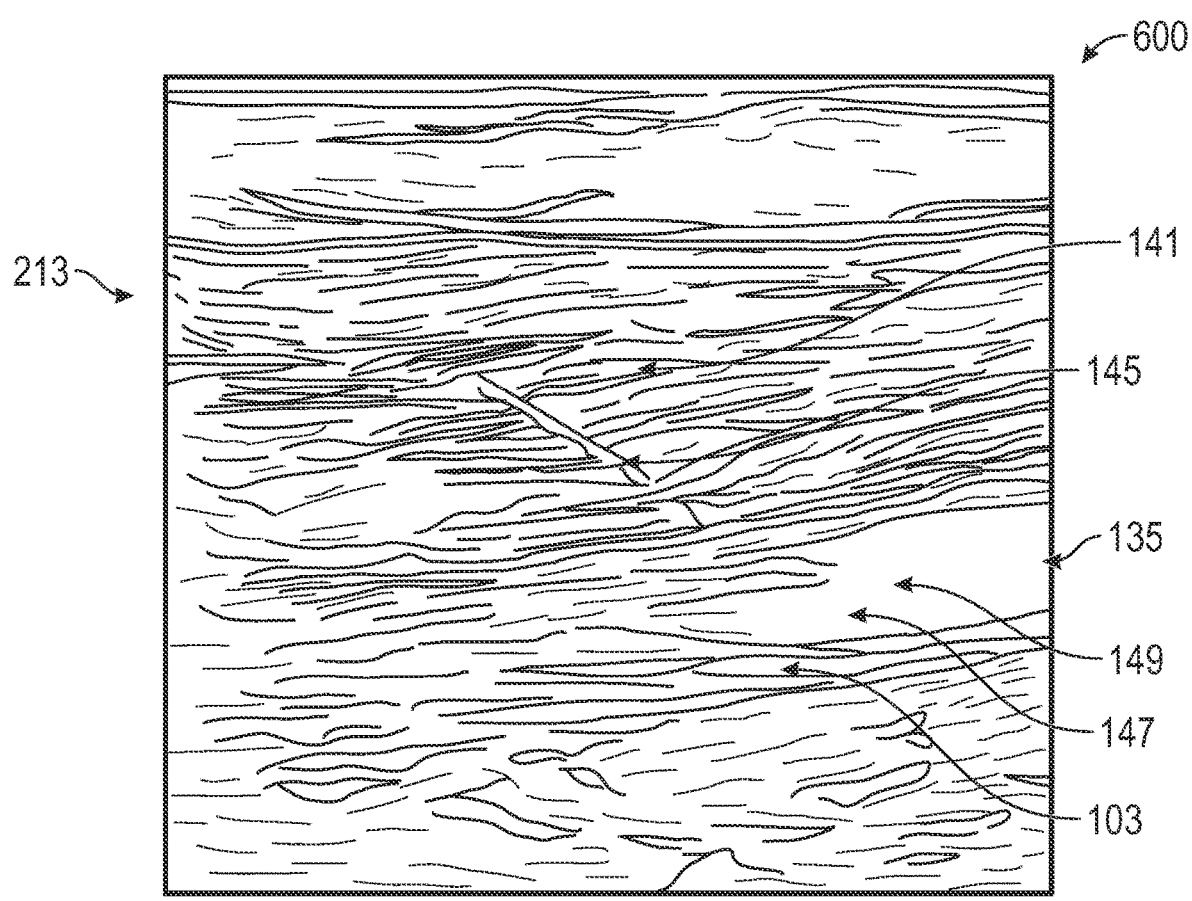
FIG. 6 is an ultrasound image of a procedure in a process of treating a compression site in accordance with aspects of the present disclosure.
Figure 7:
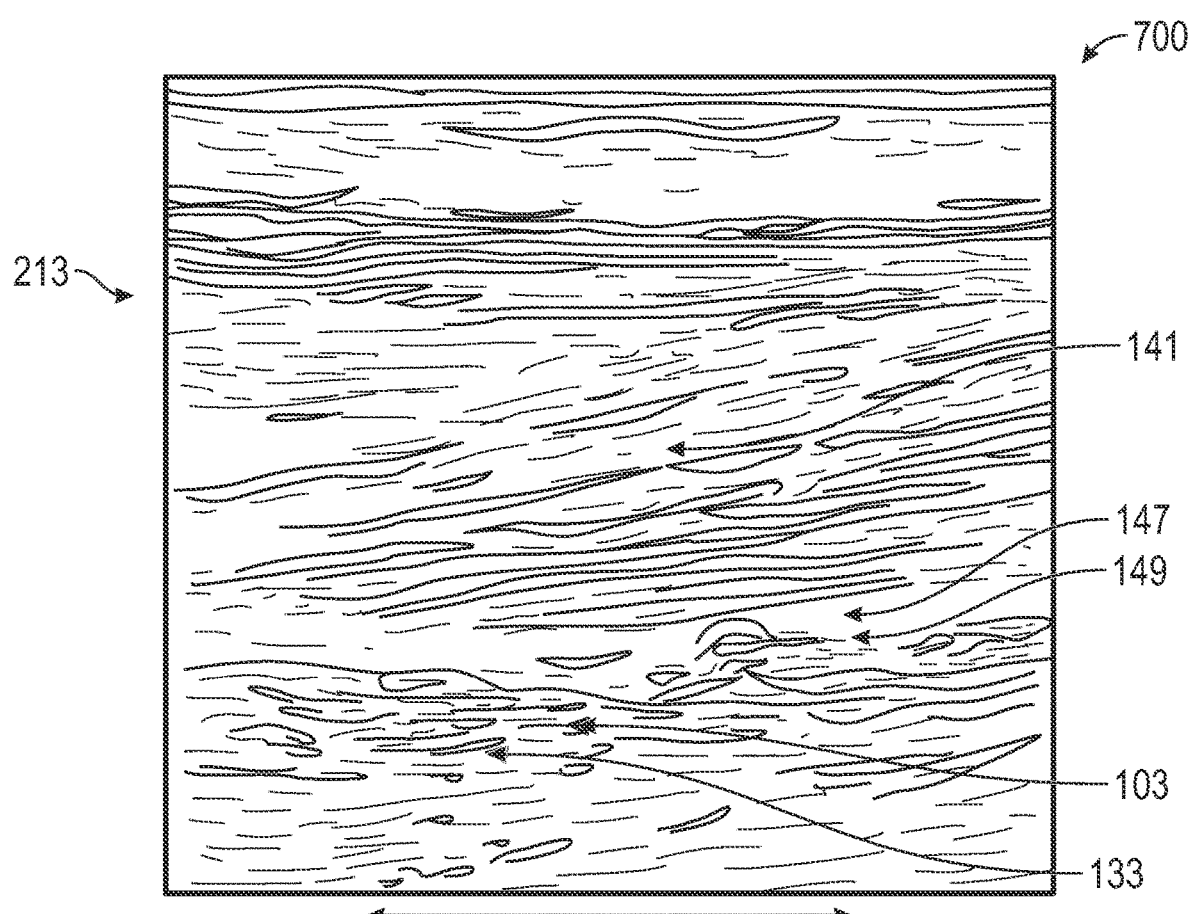
FIG. 7 is an ultrasound image of a procedure in a process of treating a compression site in accordance with aspects of the present disclosure.
Figure 8A:
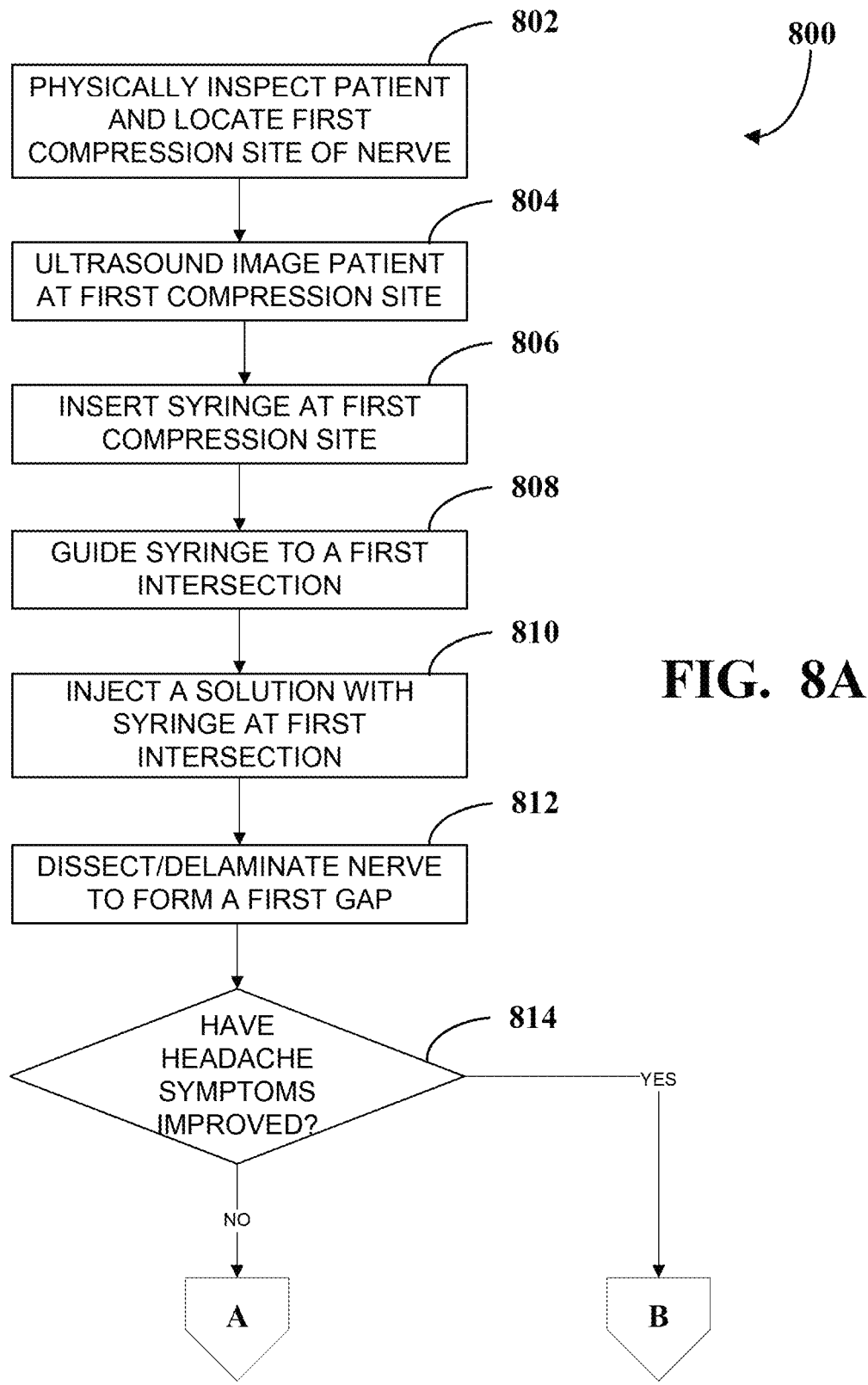
FIGS. 8A-E illustrate a flow diagram of exemplary methods for a treatment of headaches in accordance with aspects of the present disclosure.
Figure 8B:
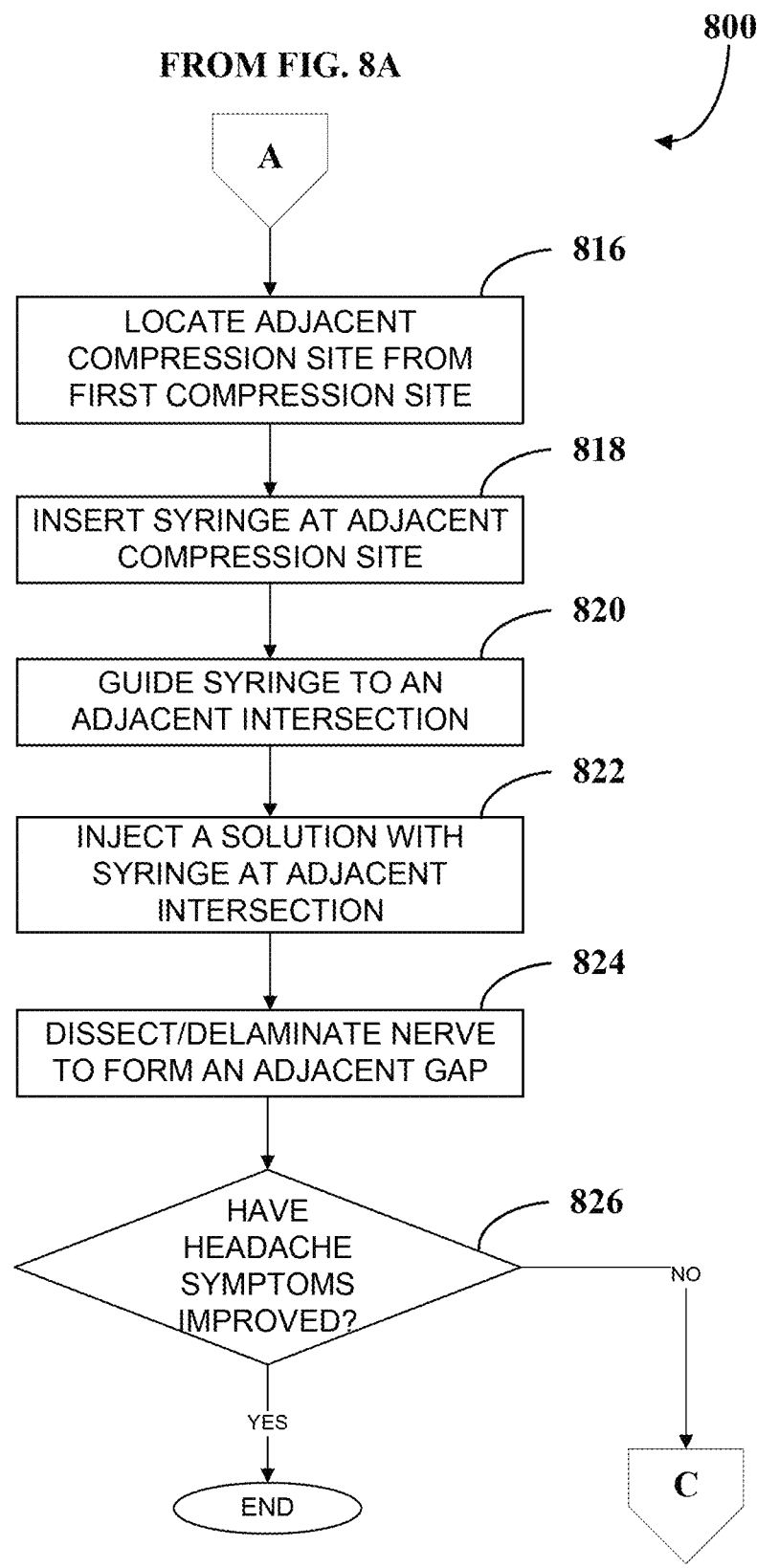
Figure 8C:
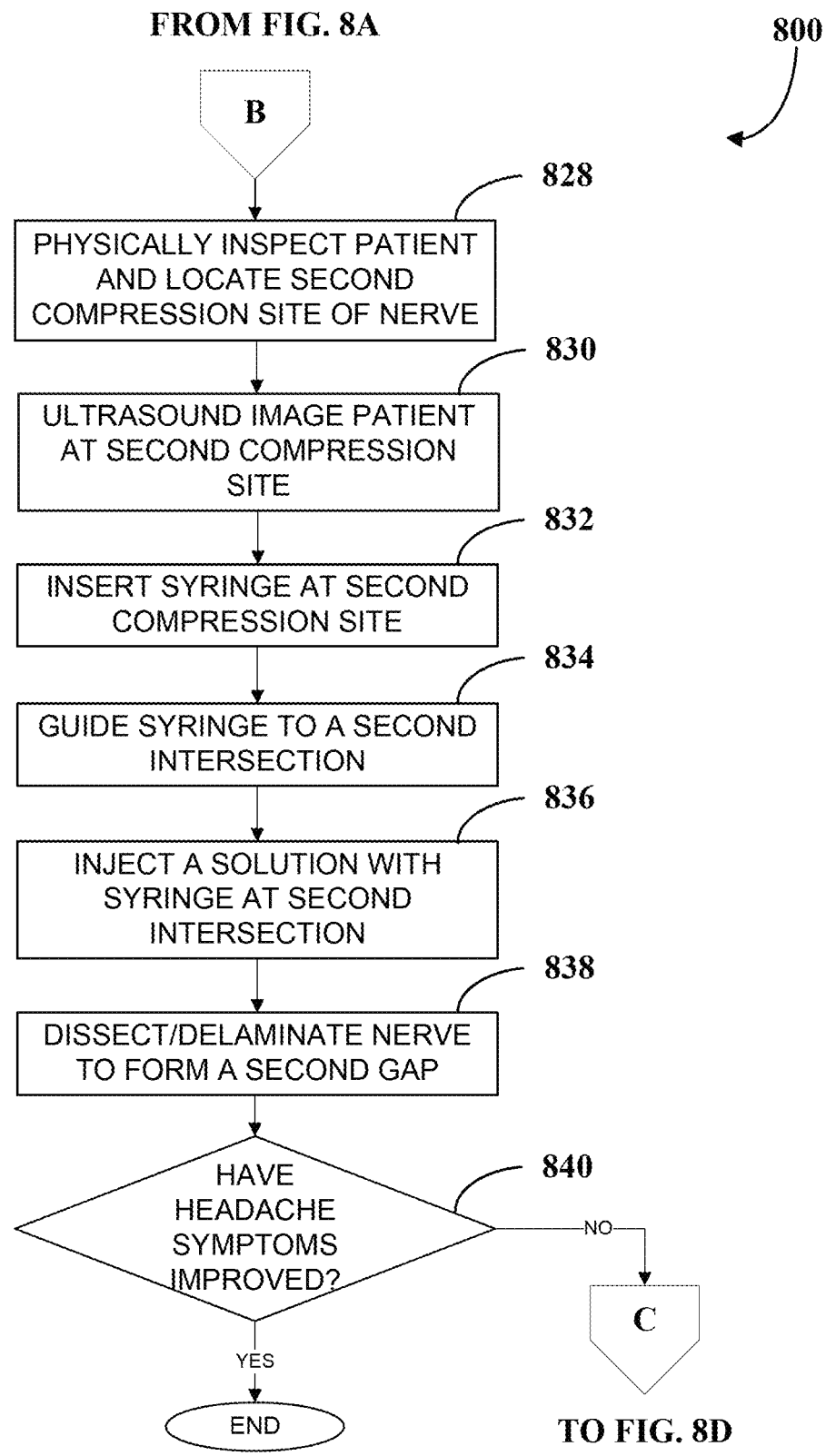
Figure 8D:
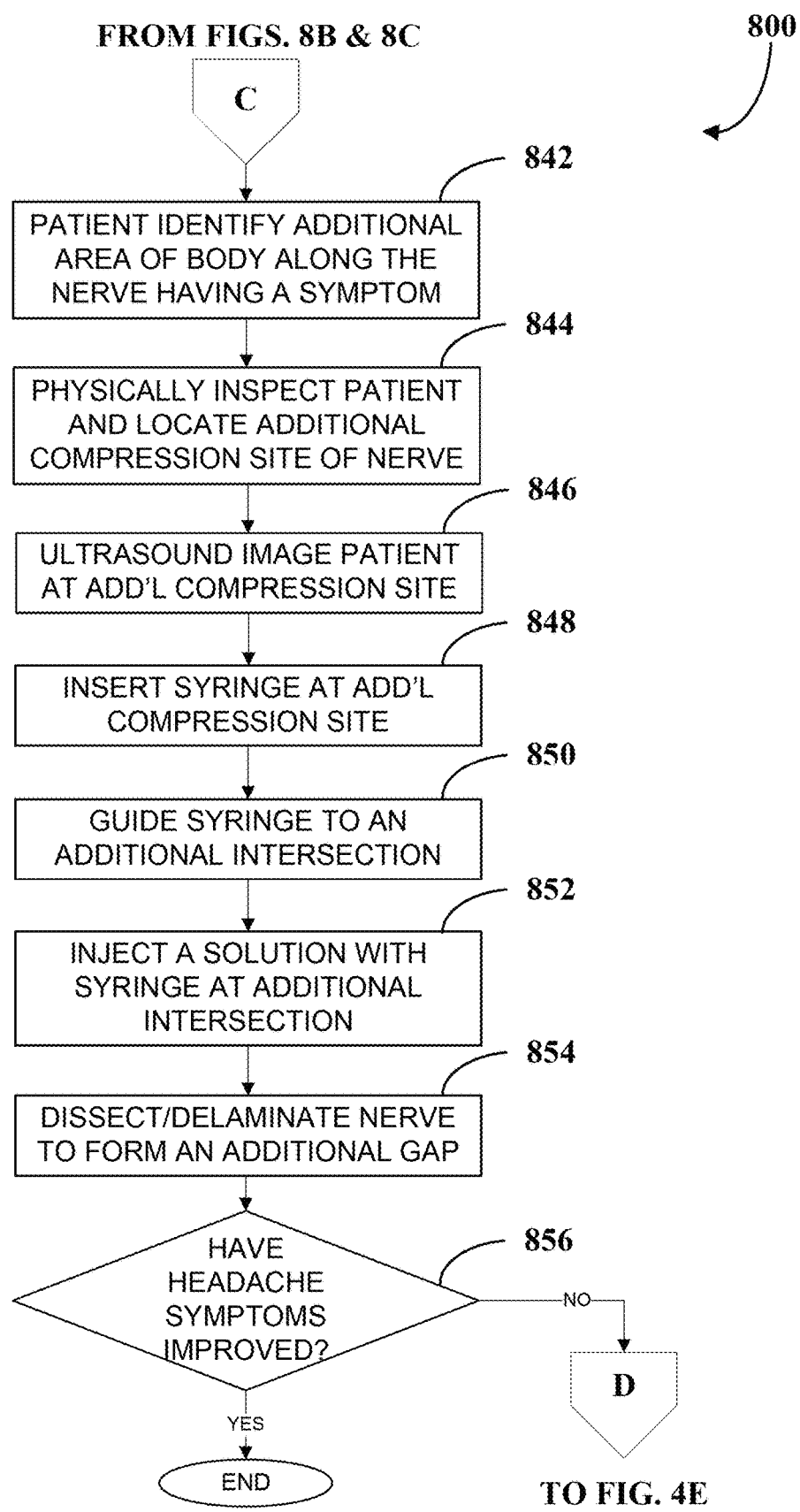
Figure 8E:
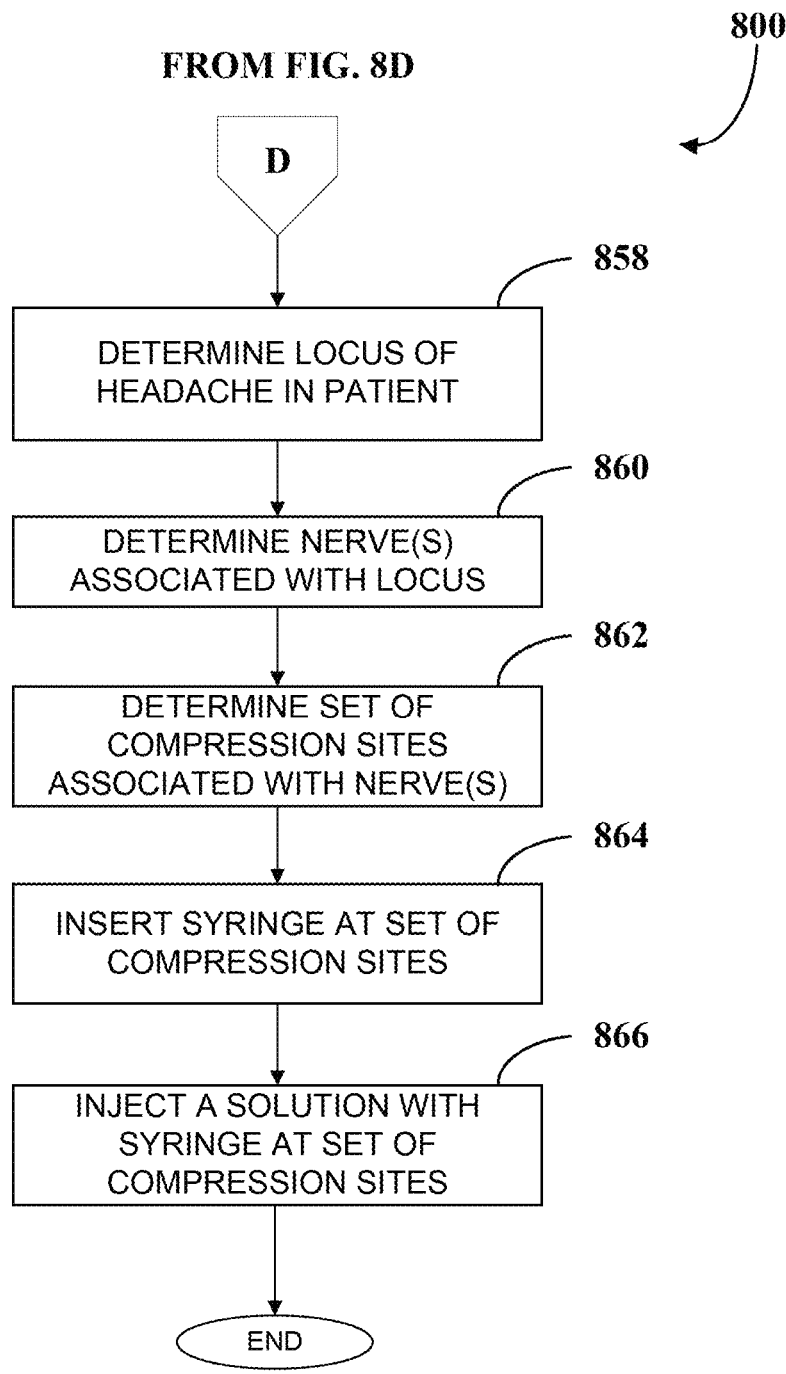

As depicted in FIG. 2, the nerve 103 passes through one of the compression sites, such as compression site 213. A fibrous ring 131 can extend through the tissue 133 of the compression site 213. The fibrous ring 131 can serve to protect the nerve 103 as it extends through the tissue 133. The tissue 133 can include muscle, fascia, ligament, or any other tissue. The nerve 103 can become inflamed and swell in or near the fibrous ring 131. The inflammation 135 (illustrated in FIG. 3) of the nerve 103 can extend beyond the fibrous ring 131 and the compression site 213.

In some embodiments, the compression sites 201-217 can be located in at least one of an arm 113, 117, shoulder 109, 111, and neck 107 of the patient 101. In other embodiments, a progression of the method can start at the hand 121 of the patient 101 and then sequentially progress in a proximal direction, relative to the patient 101, to follow the nerve 103 through the wrist 119, forearm 117, elbow 115, upper arm 113, shoulder 109, shoulder blade 111 (FIG. 1A), and neck 107 of the patient 101, or any other desired order.

Embodiments of the method can include physically inspecting (e.g., palpating) a patient 101 and locating a first compression site 213 of the nerve 103 of the patient 101. The first compression site 213 can be located where the nerve 103 passes through the tissue 133 and the nerve 103 is inflamed (e.g., at inflammation 135). In some embodiments, the method includes imaging the patient 101 at the first compression site 213, such as with ultrasound imaging. Other imaging techniques also can be used, such as magnetic resonance imaging (Mill) or any other desired technique.

Ultrasound images 400, 500, 600, 700 illustrate example images of the patient 101 during various stages of a method. In the ultrasound image 400 of FIG. 4, the tissue 133 includes muscle 141 and fascia lining, such as fascia 143. The nerve 103 is inflamed and effectively laminated with the fascia 143. Embodiments of the method can include inserting a syringe 145 (FIG. 5, ultrasound image 500) at a first injection site 137 at the first compression site 213 while the first compression site 213 is being imaged, as shown. The method can further include guiding the syringe 145 to an intersection between the nerve 103 and, in this case, the fascia 143. The method can further include injecting a solution with the syringe 145 at the intersection and dissecting or delaminating (see progression between FIGS. 6 and 7, ultrasound images 600, 700) the nerve 103 from the, in this case, the fascia 143 to form a gap 147 therebetween. The method also can include confirming with the patient 101 whether a headache symptom has changed.

Versions of the solution can include various compositions of fluid. For example, a solution 149 can comprise of dextrose 5% in water (D5W). The D5W can be used to treat inflammation 135. In another example, the solution 149 can consist only of dextrose 5% in water (D5W). In still other versions, the solution 149 can include at least one of saline and anesthetic. For example, the anesthetic can include lidocaine 1%, or any other desired anesthetics. In some embodiments, the solution 149 can include no more than about 10% of the anesthetic. The method also can include injecting a selected volume of the solution 149 into the patient 101. For example, the selected volume can be at least about five (5) cc, and can be not greater than about ten (10) cc of the solution 149. Alternatively, the selected volume can be in any range between either of these values, or any other desired values.

Each of the previously described procedures can be repeated for a second compression site 211 of the nerve 103. For example, the first compression site 213 can be located at a selected distance D (e.g., as illustrated in FIG. 2) from the second compression site 211. In some embodiments, the selected distance D can be approximately one cm, more than one cm, less than one cm, one or more inches, or any other desired distance. Some embodiments of the method include treating the first and second compression sites 213, 211 in only an appendage of the patient 101, or any other desired location. In other example, the second compression site 211 is proximal to the first compression site 213 relative to the patient 101.

In some embodiments, a length L (e.g., illustrated in FIG. 7) of the dissection of the nerve 103 from the tissue 133 can be in a selected range. For example, the length L can be at least about one (1) cm. In other examples, the length L can be not greater than about five (5) cm. Alternatively, the length L can be in any range between either of these values, or any other desired values. Each compression site can have multiple injection sites, such as two or three, depending on the length (L) of the inflammation 135 of the nerve 101. The entire length of the inflammation 135 of the nerve 103 can be treated.

In some embodiments, one or more additional insertions or injections of solution 149 can be required at each compression site. For example, the injecting procedure described herein can be repeated at a second injection site 139 (e.g., illustrated in FIG. 3). The second injection site 139 for the first compression site 213 can be adjacent to the first injection site 137 for the first compression site 213 at a selected distance D away from the first injection site 137. Injecting solution at the second injection site 139 can further dissect the nerve 103 at the first compression site 213. In some embodiments, the selected distance D can be at least about 0.5 cm, and can be not greater than about five (5) cm. Alternatively, the selected distance D can be in any range between either of these values or any other desired values.

Embodiments of the method can include performing other actions after performing the previously described procedures. For example, the method can further include prompting or asking the patient to identify any other area of the body along the nerve having another symptom, such as a headache symptom, and then repeating the treatment at the any desired area of the body identified by the patient.

Alternative embodiments of the method can include other procedures. For example, the method can further include determining a locus of the headache in the patient. The method can include determining one or more nerves associated with the locus of the headache. The method can include determining a set of compression sites that are associated with the one or more nerves. The method can include injecting the solution into the determined set of compression sites. In another embodiment, the one or more nerves associated with the locus of the headache can travel through the associated compression sites.

Embodiments of the method can further comprising repeating some or all of the prescribed procedures after an interval of time. For example, some patients can receive improved headache relief by repeating this treatment or procedure after one week. In other embodiments, some patients can receive improved headache relief by repeating the procedure at least about one time per week for at least about one week to about eight weeks, or any other desired time.

FIGS. 8A-E illustrate flow diagrams of a method 800 for the prevention and/or treatment of headaches according to embodiments of this disclosure. In this embodiment, the method 800 can be performed on a patient 101 by a doctor or any other desired healthcare professional.

Beginning at block 802, when, for example, after the doctor has determined that the patient 101 is a candidate for injections to remedy headache symptoms, the doctor can physically inspect a patient 101. The doctor can locate a first compression site 213 of a nerve 103 of the patient 101. At the first compression site 213, the nerve 103 passes through a tissue 133, such as a muscle 141, fascia 143, ligament, or any other desired tissue. The nerve 103 can be inflamed at the first compression site 213. Then, at block 804, ultrasound images of the patient 101 at the first compression site 213 are taken.

At block 806, a syringe 145 can be inserted at the first compression site 213. The syringe 145 can be inserted while the first compression site 213 is being imaged.

At block 808, the syringe 145 can be guided to an intersection (e.g., a first intersection) between the nerve 103 and the tissue 133. At block 810, a solution 149, such as D5W, can be injected using the syringe 145 at the intersection. At block 812, nerve 103 can be dissected or delaminated to form a gap 147 (e.g., a first gap).

At decision block 814, the doctor can take different courses of action based on how the patient 101 is responding to the treatment. The end result of this choice can include another form of further treatment.

If the headache symptoms have improved, then then the doctor can proceed to block 828 (discussed in more detail below). If the headache symptoms of the patient 101 have not improved, the doctor can repeat some of the previous steps at least one more time for the first compression site 213. The repeated steps can be administered adjacent to the first injection site 137 for the first compression site 213 at a selected distance away D from the first injection site 137. In doing so, the nerve 103 can be further dissected at the first compression site 213.

More specifically, at block 816, the doctor can locate an adjacent compression site from the first compression site 213. At block 818, the doctor can insert the syringe 145 at the adjacent compression site. At block 820, the doctor can guide the syringe 145 to an adjacent intersection. At block 822, the doctor can inject the patient 101 with the solution 149 at the adjacent intersection. At block 824, the doctor can dissect or delaminate the nerve 103 to form an adjacent gap. At decision block 826, the doctor can take different courses of action based on how the patient 101 is responding to the treatment. If the headache symptoms have improved, then the treatment (e.g., method 800) can end. If the headache symptoms have not improved, then the doctor can proceed to block 842.

If the headache symptoms of the patient have improved after the methods described in blocks 802-812, then at block 828, the doctor can repeat blocks 802-812 for a second compression site 211 of the nerve 103. Other compression sites also can be treated. At block 828, the patient can be physically inspected and a second compression site 211 of the nerve 103 can be located. At block 830, ultrasound images can be produced at the second compression site 211 of the patient 101. At block 832, the syringe 145 can be inserted at the second compression site 211. At block 834, the syringe 145 can be guided to a second intersection. At block 836, the solution 149 can be injected into the patient 101 at a second intersection (e.g., between the nerve 103 and the tissue 133). At block 838, the nerve can be dissected or delaminated to form a second gap between the nerve 103 and the tissue 133 (e.g., the muscle 141, the fasica 143, ligaments, or any other desired tissue). If the headache symptoms have improved, then the treatment (e.g., method 800) can end. If the headache symptoms have not improved, then the method 800 can proceed to block 842.

At this point, an initial treatment can be finished. The patient can be allowed to recover and monitored for progress. At decision blocks 826 and 840, the doctor can take different courses of action based on how the patient 101 is responding. The end result of this choice can include another form of further treatment. If the headache symptoms have improved, the method 800 can end. If the headache symptoms have not improved, at block 842, the doctor can ask the patient 101 to identify any additional area of the body of the patient 101 along a nerve having another symptom, and blocks 802-812 can be repeated at the additional area of the body of the patient 101.

For example, at block 844, the patient 101 is physically inspected and an additional compression site is located. At block 846, an ultrasound image of the patient 101 is taken at the additional compression site. At block 848, a syringe 145 is inserted at the at the additional compression site. At block 850, the syringe 145 is guided to an additional intersection, for example, between the nerve 103 and the tissue 133. At block 852, the solution 149 can be injected using a syringe 145 at the additional intersection. At block 854, the nerve 103 is dissected or delaminated to form an additional gap.

At decision block 856, a check-up is performed on the patient 101 to determine whether the patient 101 has responded positively to the treatment and, if so, whether the patient 101 needs further treatment. If the patient 101 has substantially stopped having headaches, then no further treatment may be necessary (or the patient 101 may decide to forego further treatment) and the method 800 ends. If the doctor determines that the patient 101 is a candidate for further treatment, and the patient 101 agrees to the treatment, then the method 800 proceeds to block 858.

At block 858, a locus of continuing headaches is determined in the patient 101. As discussed above, this may be facilitated by the already-performed treatment, as it is likely that the treatment will have had some therapeutic effect, which may have reduced the severity of the headache.

At block 860, one or more nerves associated with the locus of the headache is determined. At block 862, a set of compression sites that are associated with the one or more nerves is determined. The one or more nerves associated with the locus of the headache can travel through the associated compression sites. At block 864, the syringe 145 can be inserted into the patient 101 at the set of compression sites. At block 866, the solution is injected into the determined set of compression sites of the patient 101. This should reduce or eliminate the headache symptoms. The method 800 ends thereafter.

FIGS. 1-8 can include additional and/or fewer components and/or steps in an alternative order and are not limited to those illustrated in this disclosure.

Although the present disclosure has been described with exemplary embodiments, various changes and modifications may be suggested to one skilled in the art. It is intended that the present disclosure encompass such changes and modifications as fall within the scope of the appended claims.

None of the description in this application should be read as implying that any particular element, step, or function is an essential element that must be included in the claim scope. The scope of patented subject matter is defined only by the claims. Moreover, none of the claims is intended to invoke 35 U.S.C. § 112(f) unless the exact words "means for" are followed by a participle.

While the disclosure has been described in connection with certain embodiments, it is to be understood that the disclosure is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A method of neurohydrodissection for reducing a perception of pain in a patient, the method comprising:
   (a) physically inspecting the patient and locating a first compression site of a nerve of the patient where the nerve passes through a tissue and is inflamed;
   (b) imaging the patient at the first compression site; and
   (c) inserting a syringe at the first compression site, wherein while the imaging the patient at the first compression site occurs, guiding the syringe to an intersection between the nerve and the tissue, injecting a solution with the syringe at the intersection and dissecting the nerve from the tissue.

2. The method of claim 1, further comprising:
   (d) confirming with the patient whether the perception of pain has changed.

3. The method of claim 2, wherein if the perception of pain is the same or has increased, further comprising:
   (e) repeating the steps (a)-(c) for a second compression site.

4. The method of claim 3, wherein the first compression site is located at a distance of about 0.5 cm to about 5 cm away from the second compression site.

5. The method of claim 3, wherein the first compression site and the second compression site are located in an appendage of the patient.

6. The method of claim 5, wherein a progression of the method starts at the appendage of the patient and sequentially progresses from a distal direction to a proximal direction relative to the patient, to follow the nerve through at least two of a hand, a wrist, a forearm, an elbow, an upper arm, a shoulder, and a neck of the patient.

7. The method of claim 3, wherein the second compression site is proximal to the first compression site relative to the patient.

8. The method of claim 2, wherein if the perception of pain is the same or has increased, further comprising:
(f) repeating the steps (a)-(c) for a third compression site of the nerve.

9. The method of claim 8, wherein the third compression site is located in a shoulder or a neck of the patient.

10. The method of claim 1, wherein a length of the neurohydrodissection of the nerve from the tissue is in a range of about 1 cm to about 5 cm.

11. The method of claim 1, wherein the imaging comprises ultrasound imaging or magnetic resonance imaging (MRI).

12. The method of claim 1, repeating the step (c) at least one more time for the first compression site but adjacent to a first injection site for the first compression site at a selected distance away from the first injection site to further dissect the nerve at the first compression site, wherein the selected distance is in a range of about 0.5 cm to about 5 cm.

13. The method of claim 1, wherein the solution comprises dextrose 5% in water (D5W).

14. The method of claim 1, further comprising:
determining a locus of the perception of pain in the patient;
determining one or more nerves associated with the locus of the perception of pain;
determining a set of compression sites that are associated with the one or more nerves,
wherein the one or more nerves associated with the locus of the perception of pain travel through the set of compression sites; and
injecting the solution into the set of compression sites.

15. The method of claim 1, wherein the perception of pain correlates with a headache.

16. A method of neurohydrodissection for reducing a perception of pain, the method comprising:
(a) physically inspecting a patient and locating a first compression site of a nerve of the patient where the nerve passes through at least one of a muscle, a fascia, and a ligament and the nerve is inflamed;
(b) imaging the patient at the first compression site;
(c) inserting a syringe at the first compression site, wherein while the imaging of the patient at the first compression site occurs, guiding the syringe to an intersection between the nerve and the at least one of the muscle, the fascia, and the ligament, injecting a solution with the syringe at the intersection and dissecting the nerve from the at least one of the muscle, the fascia, and the ligament; and
(d) repeating the steps (a)-(c) for a second compression site.

17. The method of claim 16, further comprising:
determining a locus of the perception of pain in the patient;
determining one or more nerves associated with the locus of the perception of pain;
determining a set of compression sites that are associated with the one or more nerves,
wherein the one or more nerves associated with the locus of the perception of pain travel through the set of compression sites; and
injecting the solution into the set of compression sites.

18. The method of claim 16, wherein the solution comprises at least one of saline and anesthetic.

19. The method of claim 18, wherein the anesthetic comprises a local anesthetic.

20. The method of claim 16, wherein the solution comprises no more than about 10% of anesthetic.

21. The method of claim 16, wherein the nerve is in a peripheral nervous system of the patient.

22. The method of claim 16, wherein the injecting comprises at least about 5 cc of the solution to no more than about 10 cc of the solution.

23. The method of claim 16, wherein the perception of pain correlates with a headache.

* * * * *